United States Patent [19]

Azerad et al.

[11] Patent Number: 4,745,236
[45] Date of Patent: May 17, 1988

[54] SYNTHESIS OF CHLOROPENTAFLUOROETHANE

[75] Inventors: Robert Azerad, Corbas; Bernard Cheminal, Brignais; Henri Mathais, Saint Didier An Mont d'Or, all of France

[73] Assignee: Atochem, Courbevoie, France

[21] Appl. No.: 931,365

[22] Filed: Nov. 14, 1986

[30] Foreign Application Priority Data

Nov. 15, 1985 [FR] France ................ 85 16951

[51] Int. Cl.$^4$ .................. C07C 17/20; C07C 19/08
[52] U.S. Cl. ...................... 570/166; 502/231
[58] Field of Search ............... 570/166, 170; 502/231

[56] References Cited

U.S. PATENT DOCUMENTS

| | | | |
|---|---|---|---|
| 2,946,828 | 7/1960 | Scherer et al. | 260/653.7 |
| 3,087,974 | 4/1963 | Hauptschein et al. | 260/653 |
| 3,258,500 | 6/1966 | Swamer et al. | 260/653.7 |
| 3,793,229 | 2/1974 | Groppelli et al. | 570/166 |
| 3,961,036 | 6/1976 | Hammer et al. | 502/231 |
| 4,605,798 | 8/1986 | Abel et al. | 570/166 |

FOREIGN PATENT DOCUMENTS

| | | |
|---|---|---|
| 832501 | 1/1970 | Canada. |
| 1443184 | 10/1968 | Fed. Rep. of Germany. |
| 117580 | 1/1976 | German Democratic Rep.. |
| 48-26729 | 4/1973 | Japan. |

OTHER PUBLICATIONS

Kirk-Othmer Encyclopedia of Chemical Technology, 3rd ed., vol. 2, p. 225.

L. Marangoni et al., Journal of Fluorine Chemistry, vol. 19, (1981/82) pp. 21-34.

M. Vecchio, Journal of Fluorine Chemistry, vol. 4 (1974), pp. 117-139.

*Primary Examiner*—J. E. Evans
*Attorney, Agent, or Firm*—Pennie & Edmonds

[57] ABSTRACT

The invention relates to a gas phase process for the manufacture of chloropentafluoroethane by the action of hydrofluoric acid on dichlorotetrafluoroethane in the presence of a catalyst, the said catalyst being prepared by reacting, in a gaseous phase, an alumina in which the sodium oxide content is below 300 ppm and the volume of the pores having a radius equal to 40 angstroms or above is greater than 0.7 cm$^3$/g, with hydrofluoric acid or with a mixture of hydrofluoric acid and of air, nitrogen or a fluorinated compound.

17 Claims, No Drawings

SYNTHESIS OF CHLOROPENTAFLUOROETHANE

TECHNICAL FIELD

The present invention relates to the manufacture of chloropentafluoroethane ($C_2F_5Cl$) by a gas phase catalysed reaction of dichlorotetrafluoroethane ($C_2F_4Cl_2$) with hydrofluoric acid (HF).

BACKGROUND ART

Chloropentafluoroethane, which is used as a solvent, propellant or refrigerant fluid, is prepared by known processes, for example from perchloroethylene, chlorine and hydrofluoric acid (East German Pat. No. 117,580) or by a gas phase reaction of trichlorotrifluoroethane $C_2F_3Cl_3$ with hydrofluoric acid in the presence of aluminium trifluoride (Japanese Publication No. 48-26,729/73).

U.S. Pat. No. 3,087,974 describes the vapor phase disproportionation of chlorofluoro compounds on a catalyst without the addition of hydrofluoric acid. The disproportionation of dichlorotetrafluoroethane takes place according to the reaction:

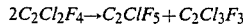

$2C_2Cl_2F_4 \rightarrow C_2ClF_5 + C_2Cl_3F_3$

This catalyst is activated alumina of high surface area which is treated with a fluorocarbon compound before being used for the disproportionation reaction. The conversion of $CF_2ClCF_2Cl$ to $C_2ClF_5$ does not exceed 34% on a molar basis and a high proportion of $C_2Cl_3F_3$ is produced as a by-product.

U.S. Pat. No. 3,258,500 describes a vapour phase catalysed fluorination using hydrofluoric acid. The dichlorotetrafluoroethane ($CF_2Cl$—$CF_2Cl$) and hydrofluoric acid (HF), in a molar ratio [HF/$CF_2Cl$—$CF_2Cl$] of between 4 and 5, react at 400° C. on a chromium oxide catalyst. The proportion of hexafluoroethane $C_2F_6$ formed is 0.19 on a molar basis relative to $C_2F_5Cl$.

A paper by L. Marangoni et al., "Preparation of chloropentafluoroethane from dichlorotetrafluoroethane" (Journal of Fluorine Chemistry 19, 1981/82, pages 21 to 34) also describes a chromium oxide-based catalyst for the gas phase manufacture of $C_2F_5Cl$ from $C_2F_4Cl_2$ and HF. The degree of conversion of $C_2Cl_2F_4$ is between 72 and 75%, the yield of $C_2F_5Cl$ is between 89 and 92%, but the formation of hexafluoroethane is still 8% on a molar basis of the formation of $C_2F_5Cl$.

A paper by M. Vecchio et al., "Studies on a vapor-phase process for the manufacture of chlorofluoroethanes" (Journal of Fluorine Chemistry, 4, 1974, pages 111 to 139) describes the same reaction as the preceding paper but on a catalyst based on aluminium fluoride doped with nickel, iron and chromium halides. The degree of conversion of $C_2F_4Cl_2$ does not exceed 41% and the molar pourcentage of $C_2F_5Cl$ at the reactor outlet is 38%.

The catalysts of the prior art are difficult to prepare, while the yields and selectivities for $C_2F_5Cl$ are mediocre.

The present invention overcomes all these disadvantages by offering a simple, flexible and economical process for producing $C_2F_5Cl$.

SUMMARY OF THE INVENTION

The invention relates to a process for synthesizing chloropentafluoro ethane which comprises reacting dichlorotetrafluoro ethane with hydrofluoric acid over a fluorinated alumina catalyst prepared from an activated alumina having a sodium oxide content below 300 ppm and a volume of the pores with a radius of 40 angstroms or above greater than 0.7 $cm^3/g$.

In this process, the reaction is carried out at a temperature range of between 350° and 550° C. at a molar ratio of hydrofluoric acid to dichlorotetrafluoro ethane of between about 0.5 and 1.5, with a reaction pressure between about 0.5 and 4 bars absolute and a reaction time of between about 5 and 15 seconds.

The fluorinated alumina catalyst is prepared by reacting the activated alumina with hydrofluoric acid or with a mixture of hydrofluoric acid and of air, nitrogen or a fluorinated compound at a sufficient temperature and pressure and for a sufficient reaction time to convert at least 70 percent by weight (preferably 90% or more) of the alumina to aluminium trifluoride.

DETAILED DESCRIPTION OF THE INVENTION

The process according to the invention includes subjecting $C_2Cl_2F_4$ to the action of HF in gaseous phase in the presence of a catalyst prepared by reacting an activated alumina in which the sodium oxide content is below 300 ppm and the volume of the pores with a radius of 40 angstroms and more is greater than 0.7 $cm^3/g$ with hydrofluoric acid or with a mixture of hydrofluoric acid and of air, nitrogen or a fluorinated compound such as, for example, dichlorotetrafluoroethane.

A high conversion, above 80%, of the starting materials and a high yield of $C_2F_5Cl$ are obtained. Another advantage of the process is increased catalyst life.

The activated aluminas are produced by controlled heating of alumina hydrates so as to remove most of the water of formation (Kirk-Othmer, Encyclopedia of Chemical Technology, 3rd edition, vol. 2, page 225).

The alumina used to prepare the catalyst is a commercially available alumina. It suffices to choose an activated alumina in which the sodium oxide content is below 300 ppm and the volume of pores with a radius equal to or greater than 40 Å is above about 0.7 $cm^3/g$ and preferably between 0.75 and 1 $cm^3/g$. It is advantageous for the alumina to be in the form of granules, beads or extrudates of a size smaller than 20 mm diameter spheres and preferably a few (i.e., 0.5-3) millimeters, to permit convenient handling during the loading and draining of the reactor.

As previously stated, the $Na_2O$ content of the alumina must be less than about 300 ppm and preferably, as low as practically possible. It is also advantageous to choose an alumina which contains, on a weight basis, not more than 0.5% of silica and 0.2% of iron oxide ($Fe_2O_3$). This alumina is converted into a mixture of at least 70%, preferably 90% or more of aluminium trifluoride ($AlF_3$), remainder unconverted alumina, by reaction with HF by itself or mixed with air, nitrogen or a fluorinated compound.

For example, it is possible to use a mixture of $C_2Cl_2F_4$ and hydrofluoric acid, which is passed over this alumina at a sufficient temperature to initiate a reaction which converts the alumina to aluminium trifluoride. It is advantageous to operate between 150° and 500° C. The operation is preferably performed at atmospheric pressure, with contact times of between 5 and 15 seconds. The specialist can easily carry out the reaction and adjust the proportions of $C_2F_4Cl_2$ and HF, the temperature, the pressure and the contact time so as to prevent the alumina being damaged by a high temperature due to the exotherm of the reaction.

When the composition of the gases no longer changes after passing over this alumina, then this indicates that the alumina has been converted to the catalyst. It can be washed with water if appropriate, before being used to effect the fluorination of $C_2F_4Cl_2$ to $C_2F_5Cl$ according to the invention.

According to a preferred embodiment of the invention the catalyst may also be prepared by subjecting alumina in a fluidized bed to the action of a stream of hot air containing hydrofluoric acid. It is advantageous to operate between 150° and 500° C. A mixture of between 0.1 and 30%, on a molar basis, of HF with air, and preferably between 1.5 and 3%, is advantageously employed. The throughput is advantageously between 200 and 250 moles/hour per liter of catalyst. The operation is preferably carried out at atmospheric pressure at temperature of 350° C. or above. It is convenient to vary the HF concentration in the air to control the exotherm of the reaction. When no more HF is consumed, the reaction is stopped and the catalyst is considered to be ready for the fluorination of $C_2F_4Cl_2$.

The reaction between $C_2F_4Cl_2$ and anhydrous HF is carried out in gaseous phase over the catalyst which may be prepared according to either of the above two routes. The reaction temperature is advantageously between 350° and 550° C. and preferably between 380° and 500° C. The molar ratio $HF/C_2Cl_2F_4$ is advantageously between 0.5 and 1.5 and preferably between 0.9 and 1.1. While the operation may be carried out at any pressure, provided that it remains in gaseous phase, it is nevertheless much simpler to operate between 0.5 and 4 bars absolute, and preferably at atmospheric pressure or thereabouts, and with a contact time of between 5 and 15 seconds and preferably between 6 and 13 seconds.

EXAMPLES

The following examples illustrate the invention without limiting it.

In all these examples, the $C_2F_4Cl_2$ employed contains 92.7% of the symmetrical isomer.

Example 1

A pure activated alumina supplied by the Kaiser Company (ref. Al 4192) in the form of 0.8 mm (1/32") extrudates is employed, the characteristics of which are as follows:

| | |
|---|---|
| Volume of pores with a radius greater than or equal to 40Å = | 0.91 cm³/g |
| Total BET specific surface = | 161 m²/g |
| Mean pore radius = | 106Å |
| Apparent density (compacted bulk) = | 0.47 |
| Surface area of pores with a radius between 50 and 250Å = | 105 m²/g |
| $Fe_2O_3$ content: 0.08% by weight | |
| $SiO_2$ content: 0.13% by weight | |
| $Na_2O$ content: 0.015% by weight. | |

0.12 liter of this alumina is charged as a fixed bed into a tubular reactor with an internal diameter of 28 mm, and it is then converted into catalyst by proceeding as in the table below.

| Temperature in the reactor (°C.) | Absolute pressure (atmospheres) | Molar throughput of reactants in moles/(hr × 100 ml of catalyst) | | Contact time (seconds) | Time (hrs) cumulative |
|---|---|---|---|---|---|
| | | $C_2Cl_2F_4$ | HF | | |
| 350 | 1 | 0.374 | 0.177 | 12.8 | 48 |
| 380 | 1 | 0.328 | 0.178 | 12.7 | 93 |
| 410 | 1 | 0.337 | 0.187 | 12.2 | 142 |

At the end of this treatment, after the oxygenfree acids have been scrubbed with water and with an aqueous sodium hydroxide solution, the proportion of $C_2ClF_5$ in the gas leaving the reactor reaches 23.6%, whereas it was only 0.7% at 350° C.

The reactor temperature is then raised to 450° C., the $C_2Cl_2F_4$ being of the same quality as before. The results are given in Table I below, where the molar throughputs are expressed per 0.1 liter of catalyst, the reactor pressure being 1 bar absolute, and the temperature being maintained at 450° C. The working time of the catalyst which is shown includes the preliminary step of conversion of alumina into catalyst.

In all the tests described above, the unconverted dichlorotetrafluoroethane (approximately 15% on a molar basis of the $C_2Cl_2F_4$ compound employed) contains 20 to 25% of the symmetrical isomer $CF_2Cl-CF_2Cl$.

After 550 hours operation under the working conditions described above, and a regeneration with pure air at 450° C., the catalyst produces results which are absolutely identical to the above.

Example 2

The same activated alumina as in Example 1, in the same physical form of 0.8 mm extrudates, is taken and is converted into catalyst by a fluidized bed technique. 0.125 liter of Kaiser 4192 alumina (51.3 g) is taken and heated to 350° C. in a stream of nitrogen, and the following gas mixture is then introduced for 24 hours at atmospheric pressure:
air: 27.2 moles/h
HF: 0.77 moles/h.

After 24 hours of this treatment, the catalyst contains 62% of fluorine, that is to say 91.4% of aluminium fluoride and 8.6% of unconverted alumina. Its weight is 77.9 grams.

68.1 grams of this catalyst (0.1 liter) are taken to be tested in the same 28 mm diameter tubular reactor as in Example 1, and the procedure of Example 1 is followed. The results are shown in Table II below.

The catalyst working time which is shown in this table corresponds to the period beginning with the charging of the reactor with a fixed bed and does not include the conversion of alumina into catalyst.

Example 3

The method of Example 2 is followed, starting with the same activated alumina, except that after the conversion of the alumina into catalyst and charging the reactor with a fixed bed for the fluorination of $C_2F_4Cl_2$, the reaction is started with a molar ratio $HF/C_2Cl_2F_4$ close to 1 instead of 0.4 in Example 2.

The results are shown in Table III.

The starting method does not alter the catalyst's activity or selectivity.

The working time shown is the period from the charging of the reactor with a fixed bed and does not include the conversion of alumina into catalyst.

Example 4 (comparative)

The procedure of Example 2 is followed but using an activated alumina whose pore volume is different from that of the activated alumina used in the process according to the invention; the alumina used is SCM 250, the characteristics of which are:

Chemical purity:
  $Na_2O$: 800 ppm
  $Fe_2O_3$: 300 ppm
  $SiO_2$: 200 ppm
Physical properties:
  Form: beads, 2 to 4 mm in diameter
  Specific surface (BET)=270 $m^2/g$
  Total volume of pores of radius greater than or equal to 40 Å=0.63 $cm^3/g$
  Mean pore diameter 90 Å
  Bulk density: 0.66 g/ml.

A catalyst is obtained whose $AlF_3$ content is 87.7% by weight, the remainder being unconverted alumina. The results are shown in Table IV,1; the working times are measured as in Example 2.

The same SCM 250 alumina is used as spheres of 2 to 4 mm and is converted into catalyst as before, but after the conversion it is reduced mechanically into small pieces of less than 1 mm to approach the size of the Kaiser alumina of Examples 1, 2 and 3. This catalyst is then used as before.

The results are shown in Table IV,2.

The working times shown in the table do not include the time for converting the alumina to catalyst.

Example 5

CS 331-1 alumina sold by the Catalysts and Chemicals Europe (CCE) company is employed.

Its chief physical characteristics are as follows:
  form: extrudates 1/16″ (1.6 mm) in diameter
  active surface area (BET): 255 $m^2/g$
  mean pore diameter: 90 Å
  volume of pores of radius greater than or equal to 40 Å: 0.76 $cm^3/g$
  bulk density: 0.60 g/ml.
  $Na_2O$: 200 ppm
  $Fe_2O_3$: 800 ppm
  $SiO_2$: 300 ppm The catalyst is prepared as in Example 2, the $AlF_3$ concentration of the catalyst is 92%, with 8% unconverted alumina.

The results of the corresponding tests are shown in Table No. V below; the results obtained are found to be clearly superior to those obtained in comparative Example No. 4 (SCM 250 alumina).

TABLE I

| | OPERATING CONDITIONS | | | | | | RESULTS OBTAINED | | | | |
|---|---|---|---|---|---|---|---|---|---|---|---|
| Catalyst working time (cumulative hours) | Molar throughput of reactants (moles/hour) | | Molar ratio HF/ $C_2Cl_2F_4$ | Contact time (seconds) | Degree of conversion % | | Degree of conversion of $C_2Cl_2F_4$ to $C_2ClF_5$ % | Molar ratio $C_2F_6$/ $C_2ClF_5$ (× 100) | Molar ratio $C_2F_3Cl_3$/ $C_2ClF_5$ (× 100) | Molar ratio $CF_4 + CF_3Cl$/ $C_2ClF_5$ (× 100) | Specific output in grams of $C_2ClF_5$ per hour per liter of catalyst |
| | HF | $C_2Cl_2F_4$ | | | HF | $C_2Cl_2F_4$ | | | | | |
| 165 | 0.132 | 0.330 | 0.40 | 13.1 | 90.0 | 76.9 | 62.0 | 0.5 | 20.1 | 0.2 | 316 |
| 257 | 0.268 | 0.257 | 1.04 | 11.6 | 79.3 | 85.2 | 81.4 | 0.6 | 3.9 | 0.1 | 310 |
| 445 | 0.254 | 0.283 | 0.90 | 11.3 | 73.1 | 85.5 | 81.7 | 0.5 | 4.0 | 0.1 | 351 |

TABLE II

| | OPERATING CONDITIONS | | | | | | RESULTS OBTAINED | | | |
|---|---|---|---|---|---|---|---|---|---|---|
| Catalyst working time (cumulative hours) | Molar throughput of reactants (moles/hour) | | Contact time (seconds) | Degree of conversion % | | Degree of conversion of $C_2Cl_2F_4$ to $C_2ClF_5$ % | Molar ratio $C_2F_6 + CF_4$/ $C_2ClF_5$ (× 100) | Molar ratio $C_2F_3Cl_3$/ $C_2ClF_5$ (× 100) | Specific output in grams of $C_2ClF_5$ per hour per liter of catalyst |
| | HF | $C_2Cl_2F_4$ | | HF | $C_2Cl_2F_4$ | | | | |
| 23.5 | 0.140 | 0.377 | 11.8 | 89.3 | 80.4 | 64.7 | 1.1 | 19.2 | 377 |
| 46.5 | 0.149 | 0.365 | 11.8 | 91.1 | 80.5 | 65.1 | 1.2 | 18.8 | 367 |
| 66.5 | 0.140 | 0.360 | 12.2 | 93.4 | 79.6 | 63.8 | 0.7 | 20.0 | 354 |
| 89.5 | 0.244 | 0.247 | 12.4 | 79.5 | 87.9 | 80.8 | 1.0 | 5.5 | 309 |
| 111.5 | 0.223 | 0.247 | 12.9 | 80.2 | 87.2 | 79.6 | 1.0 | 6.0 | 304 |
| 133.5 | 0.218 | 0.247 | 13.0 | 83.1 | 85.8 | 77.2 | 1.0 | 7.5 | 295 |

Operating conditions
Fixed bed catalyst (volume = 0.1 liter)
Temperature: 450° C.
Pressure: atmospheric

TABLE III

| | OPERATING CONDITIONS | | | | | RESULTS OBTAINED | | | |
|---|---|---|---|---|---|---|---|---|---|
| Catalyst working time (cumulative hours) | Molar throughput of reactants (moles/hour) | | Molar ratio HF/ $C_2Cl_2F_4$ | Contact time (seconds) | Degree of conversion % | | Degree of conversion of $C_2Cl_2F_4$ to $C_2ClF_5$ % | Molar ratio $C_2F_6 + CF_4/$ $C_2ClF_5$ (× 100) | Molar ratio $C_2F_3Cl_3/$ $C_2ClF_5$ (× 100) | Specific output in grams of $C_2ClF_5$ per hour per liter of catalyst |
| | HF | $C_2Cl_2F_4$ | | | HF | $C_2Cl_2F_4$ | | | | |
| 24 | 0.255 | 0.243 | 1.05 | 13.2 | 75.4 | 86.5 | 79.8 | 1.2 | 4.5 | 300 |
| 47 | 0.240 | 0.245 | 0.98 | 12.5 | 76.8 | 86.7 | 79.9 | 0.9 | 5.2 | 302 |

Operating conditions
Fixed bed catalyst (volume = 0.1 liter) prepared as in Example No. 2
Temperature = 450° C.
Pressure: atmospheric

TABLE IV,1

| | OPERATING CONDITIONS | | | | | RESULTS OBTAINED | | | |
|---|---|---|---|---|---|---|---|---|---|
| Catalyst working time (cumulative hours) | Molar throughput of reactants (moles/hour) | | Molar ratio HF/ $C_2Cl_2F_4$ | Contact time (seconds) | Degree of conversion % | | Degree of conversion of $C_2Cl_2F_4$ to $C_2ClF_5$ % | Molar ratio $C_2F_6 + CF_4/$ $C_2ClF_5$ (× 100) | Molar ratio $C_2F_3Cl_3/$ $C_2ClF_5$ (× 100) | Specific output in grams of $C_2ClF_5$ per hour per liter of catalyst |
| | HF | $C_2Cl_2F_4$ | | | HF | $C_2Cl_2F_4$ | | | | |
| 24 | 0.240 | 0.243 | 0.99 | 12.5 | 9.0 | 9.4 | 6.8 | 5.8 | 4.3 | 25 |
| 48 | 0.235 | 0.253 | 0.93 | 12.4 | 10.0 | 10.3 | 8.2 | 2.4 | 3.6 | 32 |
| 71 | 0.249 | 0.253 | 0.98 | 12.1 | 12.7 | 10.3 | 7.9 | 1.9 | 3.7 | 31 |

Operating conditions common to the tests
Fixed bed catalyst (volume = 0.1 liter) in the form of 2 to 4 mm beads
Temperature = 450° C.
Atmospheric pressure

TABLE IV,2

| | OPERATING CONDITIONS | | | | | RESULTS OBTAINED | | | |
|---|---|---|---|---|---|---|---|---|---|
| Catalyst working time (cumulative hours) | Molar throughput of reactants (moles/hour) | | Molar ratio HF/ $C_2Cl_2F_4$ | Contact time (seconds) | Degree of conversion % | | Degree of conversion of $C_2Cl_2F_4$ to $C_2ClF_5$ % | Molar ratio $C_2F_6 + CF_4/$ $C_2ClF_5$ (× 100) | Molar ratio $C_2F_3Cl_3/$ $C_2ClF_5$ (× 100) | Specific output in grams of $C_2ClF_5$ per hour per liter of catalyst |
| | HF | $C_2Cl_2F_4$ | | | HF | $C_2Cl_2F_4$ | | | | |
| 117 | 0.232 | 0.233 | 1.0 | 13.0 | 9.5 | 10.6 | 8.4 | 0.6 | 2.3 | 30 |
| 139 | 0.239 | 0.234 | 1.0 | 12.8 | 8.9 | 10.3 | 8.0 | 0.6 | 2.4 | 29 |
| Temperature = 500° C. after the 139th hour | | | | | | | | | | |
| 159 | 0.238 | 0.230 | 1.0 | 12.1 | 10.9 | 20.3 | 17.2 | 1.5 | 1.1 | 61 |

Operating conditions
Fixed bed catalyst (volume = 0.1 liter)
Temperature = 450° C. up to the 139th hour, then 500° C.
Atmospheric pressure

TABLE V

| | OPERATING CONDITIONS | | | | | RESULTS OBTAINED | | | |
|---|---|---|---|---|---|---|---|---|---|
| Catalyst working time (cumulative hours) | Molar throughput of reactants (moles/hour) | | Molar ratio HF/ $C_2Cl_2F_4$ | Contact time (seconds) | Degree of conversion % | | Degree of conversion of $C_2Cl_2F_4$ to $C_2ClF_5$ % | Molar ratio $C_2F_6 + CF_4/$ $C_2ClF_5$ (× 100) | Molar ratio $C_2F_3Cl_3/$ $C_2ClF_5$ (× 100) | Specific output in grams of $C_2ClF_5$ per hour per liter of catalyst |
| | HF | $C_2Cl_2F_4$ | | | HF | $C_2Cl_2F_4$ | | | | |
| 25 | 0.245 | 0.242 | 1.0 | 12.5 | 67.7 | 76.9 | 71.5 | 1.7 | 5.3 | 268 |
| 48 | 0.245 | 0.245 | 1.0 | 12.4 | 66.4 | 77.0 | 71.0 | 1.0 | 5.4 | 268 |
| 71 | 0.245 | 0.245 | 1.0 | 12.4 | 66.8 | 76.9 | 70.7 | 1.0 | 5.7 | 268 |
| 86.5 | 0.194 | 0.243 | 0.8 | 13.9 | 66.2 | 78.3 | 70.8 | 1.2 | 7.5 | 266 |

Operating conditions
Fixed bed catalyst (volume = 0.1 liter) in the form of 1.6 mm extrudates, prepared as in Example No. 2
Temperature = 450° C.
Atmospheric pressure

TABLE VI

| Catalyst working time (cumulative hours) | Molar throughput of reactants (moles/hour) HF | Molar throughput of reactants (moles/hour) $C_2Cl_2F_4$ | Molar ratio HF/$C_2Cl_2F_4$ | Contact time (seconds) | Degree of conversion % HF | Degree of conversion % $C_2Cl_2F_4$ | Degree of conversion of $C_2Cl_2F_4$ to $C_2ClF_5$ % | Molar ratio $C_2F_6 + CF_4/C_2ClF_5$ (× 100) | Molar ratio $C_2F_3Cl_3/C_2ClF_5$ (× 100) | Specific output in grams of $C_2ClF_5$ per hour per liter of catalyst |
|---|---|---|---|---|---|---|---|---|---|---|
| 24 | 0.357 | 0.358 | 1.0 | 11.8 | 7.0 | 0.2 | 0.1 | 0 | 0 | 0.4 |
| 47 | 0.351 | 0.378 | 0.9 | 11.6 | 2.0 | 0.1 | 0.1 | 0 | 0 | 0.4 |
| 70 | 0.351 | 0.376 | 0.9 | 11.6 | 4.1 | 0.1 | 0.1 | 0 | 0 | 0.4 |
| 92 | 0.360 | 0.368 | 1.0 | 10.8 | 5.4 | 0.2 | 0.1 | 0 | 0 | 0.4 |

Operating conditions
Catalysts in the form of a fluid bed (volume = 0.14 liter) with a mean particle size of 50 to 80 microns
Temperature = 450° C.
Atmospheric pressure

TABLE VII

| Catalyst working time (cumulative hours) | Molar throughput of reactants (moles/hour) HF | Molar throughput of reactants (moles/hour) $C_2Cl_2F_4$ | Molar ratio HF/$C_2Cl_2F_4$ | Contact time (seconds) | Degree of conversion % HF | Degree of conversion % $C_2Cl_2F_4$ | Degree of conversion of $C_2Cl_2F_4$ to $C_2ClF_5$ % | Molar ratio $C_2F_6 + CF_4/C_2ClF_5$ (× 100) | Molar ratio $C_2F_3Cl_3/C_2ClF_5$ (× 100) | Specific output in grams of $C_2ClF_5$ per hour per liter of catalyst |
|---|---|---|---|---|---|---|---|---|---|---|
| 24 | 0.349 | 0.375 | 0.93 | 8.4 | 60.3 | 65.4 | 60.2 | 1.0 | 7.5 | 348.8 |
| 48 | 0.367 | 0.373 | 0.98 | 8.2 | 59.5 | 67.2 | 62.5 | 0.5 | 7.0 | 360.2 |
| 72.45 | 0.521 | 0.501 | 1.04 | 5.9 | 51.7 | 60.9 | 57.1 | 0.5 | 6.1 | 442.0 |
| 95.45 | 0.500 | 0.495 | 1.01 | 6.4 | 54.4 | 62.7 | 58.5 | 0.7 | 6.7 | 447.4 |

Operating conditions
Fixed bed catalysts (volume = 0.1 liter) in the form of 0.8 mm extrudates
Temperature = 450° C.
Atmospheric pressure

TABLE VIII

| $Na_2O$ content (ppm) | Molar throughput of reactants (moles/hour) HF | Molar throughput of reactants (moles/hour) $C_2Cl_2F_4$ | Molar ratio HF/$C_2Cl_2F_4$ | Contact time (seconds) | Degree of conversion % HF | Degree of conversion % $C_2Cl_2F_4$ | Degree of conversion of $C_2Cl_2F_4$ to $C_2ClF_5$ (%) | Molar ratio $C_2Cl_3F_3/C_2ClF_5$ (× 100) | Specific output in grams of $C_2ClF_5$ per hour per liter of catalyst |
|---|---|---|---|---|---|---|---|---|---|
| 150 | 0.449 | 0.429 | 1.05 | 7.4 | 52.1 | 61.1 | 57.9 | 5.5 | 383.8 |
| 930 | 0.411 | 0.428 | 0.96 | 7.2 | 7.8 | 8.1 | 7.7 | 5.2 | 50.9 |

Operating conditions
Fixed bed catalysts (volume = 0.1 liter) in the form of 0.8 mm extrudates
Temperature = 450° C.
Atmospheric pressure The working times shown do not include the conversion of alumina into catalyst.

Example 6 (comparative)

Fluorination of $C_2F_4Cl_2$ with HF according to a process not in accordance with the invention.

Instead of taking an alumina and converting it into catalyst as previously, a commercial aluminium trifluoride powder containing approximately 8% of alumina is used.

Its chief physicochemical characteristics are as follows:
 mean particle size of the powder: 50 to 80 microns
 total specific area (BET) = 1.6 m²/g
 volume of pores of radius greater than or equal to 40 Å: 0.25 cm³/g.

After this, the procedure is as in the preceding examples of the fluorination of $C_2F_4Cl_2$ with HF, but in a fluid bed instead of a fixed bed.

The results appear in Table VI.

Example 7

The procedure of Example 2 is followed, using the same type of alumina (Kaiser 4192), but working with a shorter contact time.

The results are shown in Table VII, where the working times do not include the time for converting the alumina into catalyst.

It is found that the specific output of $C_2ClF_5$ can be considerably increased without harming the yield.

Table VIII collates results obtained under analogous operating conditions and shows the effect of the $Na_2O$ content.

While it is apparent that the invention herein disclosed is well calculated to fulfill the desired results, it will be appreciated that numerous modifications and embodiments may be devised by those skilled in the art, and it is intended that the appended claims cover all such modifications and embodiments as fall within the true spirit and scope of the present invention.

What is claimed is:

1. A process for the manufacture of chloropentafluoroethane which comprises subjecting dichlorotetrafluoroethane to the action of hydrofluoric acid in gaseous phase in the presence of a fluorinated alumina catalyst, said catalyst being prepared by reacting in gaseous phase an activated alumina in which the sodium oxide content is below 300 ppm and the volume of the pores having a radius of 40 angstroms or above is greater than 0.7 cm$^3$/g, with hydrofluoric acid or with a mixture of hydrofluoric acid and of air, nitrogen or a fluorinated compound.

2. The process of claim 1 wherein the fluorinated alumina catalyst is prepared from an alumina in which the volume of the pores having a radius of 40 angstroms or above is between 0.75 and 1 cm$^3$/g.

3. The process of claim 1 wherein the fluorinated alumina catalyst is prepared from an alumina containing less than 0.5 weight percent silica and less than 0.2 weight percent iron oxide.

4. The process of claim 1 wherein the fluorinated alumina catalyst is prepared from an alumina in the form of particles having sizes smaller than 20 mm diameter spheres.

5. The process of claim 1 wherein the fluorinated alumina catalyst is prepared by reacting the alumina with a mixture of air and hydrofluoric acid at a temperature of between 150° and 500° C.

6. The process of claim 5 wherein the molar proportion of hydrofluoric acid in the mixture air-HF is between about 0.1 and 30 percent.

7. The process of claim 5 wherein the molar proportion of hydrofluoric acid in the mixture air-HF is between about 1.5 and 3 percent.

8. The process of claim 5 wherein the reaction is effected at atmospheric pressure and at a temperature of 350° C. or above.

9. The process of claim 1 wherein the fluorinated alumina catalyst is prepared by passing over the alumina a gaseous mixture of hydrofluoric acid and dichlorotetrafluoroethane at a temperature of between 150° and 500° C.

10. The process of claim 9 wherein the operation is effected at atmospheric pressure with a contact time of between about 5 and 15 seconds.

11. A process for the manufacture of chloropentafluoroethane which comprises:

preparing a fluorinated alumina catalyst by reacting an activated alumina having a sodium oxide content below 300 ppm and a volume of the pores with a radius of 40 angstroms or above greater than 0.7 cm$^3$/g, with a mixture of air and hydrofluoric acid at a temperature of between about 150° and 500° C. and atmospheric pressure, until no more HF is consumed; and passing over this catalyst hydrofluoric acid and dichlorotetrafluoroethane at a temperature of between about 350° and 550° C. and a pressure of between about 0.5. and 4 bars absolute for a contact time of between about 5 and 15 seconds.

12. The process of claim 11 wherein the molar ratio of hydrofluoric acid to dichlorotetrafluoroethane is between about 0.5 and 1.5.

13. The process of claim 11 wherein the reaction pressure is atmospheric.

14. A process for the manufacture of chloropentafluoroethane which comprises:

preparing a fluorinated alumina catalyst by reacting an activated alumina having a sodium oxide content below 300 ppm and a volume of the pores with a radius of 40 angstroms or above greater than 0.7 cm$^3$/g, with a gaseous mixture of hydrofluoric acid and dichlorotetrafluoro ethane at a temperature of between about 150° and 500° C. and atmospheric pressure, until the composition of the outgoing gases no longer changes; and passing over this catalyst hydrofluoric acid and dichlorotetrafluoroethane at a temperature of between about 350° and 500° C. and a pressure of between about 0.5 and 4 bars absolute for a contact time of between about 5 and 15 seconds.

15. The process of claim 14 wherein the reaction pressure is atmospheric.

16. The process of claim 14 wherein the molar ratio of hydrofluoric acid to dichlorotetrafluoroethane is between about 0.5 and 1.5.

17. A process for the manufacture of chloropentafluoroethane which comprises:

preparing a fluorinated alumina catalyst by reacting an activated alumina in the form of particles having a size smaller than 20 mm diameter spheres and having a sodium oxide content below 300 ppm, a silica content of less than 0.5 weight percent, an iron oxide content of less than 0.2 weight percent, and a volume of the pores with a radius of 40 angstroms of above greater than 0.7 cm$^3$/g, with a gaseous mixture of hydrofluoric acid and a fluorinated compound wherein the weight ratio of hydrofluoric acid to the fluorinated compound is between about 0.5 and 1.5 at a temperature of between about 150° and 500° C. and atmospheric pressure to convert at least 70% by weight of the alumina to aluminum trifluoride, and passing over this catalyst hydrofluoric acid and dichlorotetrafluoroethane at a temperature of between about 350° and 500° C. and a pressure of between about 0.5 and 4 bars absolute for a contact time of between about 5 and 15 seconds to form chloropentafluoroethane at a rate of conversion of at least about 80%.

* * * * *